United States Patent
Weber et al.

(10) Patent No.: US 9,475,738 B2
(45) Date of Patent: Oct. 25, 2016

(54) METHODS AND APPARATUS FOR DEACTIVATING A CATALYST COMPOSITION

(75) Inventors: Michael W. Weber, Houston, TX (US); James R. Lattner, LaPorte, TX (US); Michael J. Veraa, Kemah, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 232 days.

(21) Appl. No.: 14/359,394

(22) PCT Filed: Aug. 23, 2012

(86) PCT No.: PCT/US2012/051956
§ 371 (c)(1),
(2), (4) Date: Jul. 15, 2014

(87) PCT Pub. No.: WO2013/095720
PCT Pub. Date: Jun. 27, 2013

(65) Prior Publication Data
US 2015/0291486 A1    Oct. 15, 2015

Related U.S. Application Data

(60) Provisional application No. 61/578,996, filed on Dec. 22, 2011.

(51) Int. Cl.
| | |
|---|---|
| *C07C 2/24* | (2006.01) |
| *B01J 8/00* | (2006.01) |
| *C07C 2/32* | (2006.01) |
| *C07C 2/30* | (2006.01) |
| *C08F 2/42* | (2006.01) |
| *B01J 19/24* | (2006.01) |

(52) U.S. Cl.
CPC ............. *C07C 2/32* (2013.01); *B01J 19/245* (2013.01); *C07C 2/30* (2013.01); *C08F 2/42* (2013.01); *B01J 2219/24* (2013.01); *C07C 2531/22* (2013.01)

(58) Field of Classification Search
CPC .......... C07C 2/30; C07C 2/32; C07C 11/02; B01J 19/245; C08F 2/42; C08F 10/02; C08F 2/24; C08F 210/16; C08F 210/14
USPC ......................................... 585/512; 422/187
See application file for complete search history.

(56) References Cited

U.S. PATENT DOCUMENTS

| | | |
|---|---|---|
| 7,157,612 B2 | 1/2007 | Ewert et al. |
| 2010/0113851 A1* | 5/2010 | Kreischer ............ B01J 31/0237 585/511 |

FOREIGN PATENT DOCUMENTS

| | | |
|---|---|---|
| WO | WO 2004/082827 | 9/2004 |
| WO | WO 2007/092136 | 8/2007 |
| WO | WO 2009/060343 | 5/2009 |

* cited by examiner

*Primary Examiner* — William Cheung

(57) ABSTRACT

Disclosed herein are methods and apparatus for deactivating a catalyst composition in an reaction product stream. One such method and apparatus contact the catalyst composition with a catalyst-deactivating composition and a diluent in a vapor phase of a product-receiving vessel, wherein the boiling point of the diluent is at least 5.0° C. greater than the boiling point of the catalyst-deactivating composition. Also disclosed are oligomerization systems for producing oligomers.

20 Claims, 4 Drawing Sheets

METHODS AND APPARATUS FOR DEACTIVATING A CATALYST COMPOSITION

PRIORITY

This application is a National Stage application of International Application No. PCT/2012/051956, filed Aug. 23, 2012, that claims the benefit of Application No. 61/578,996, filed Dec. 22, 2011, the disclosures of which are hereby incorporated by reference in their entireties.

FIELD

The present invention relates to methods of deactivating a catalyst, particularly a catalyst in an oligomerization reaction, and oligomerization processes employing such methods.

BACKGROUND

Many chemical processes are catalytically activated to convert less valuable feed components into more valuable products. For example, 1-hexene can be produced in high selectivity via ethylene trimerization using homogeneous, single-site chromium catalyst systems, activated by a molar excess of alkyl aluminums such as methyl alumoxane (MAO) and modified methyl alumoxane (MMAO). 1-Hexene has many potential uses, one of which is as a comonomer in higher order polyolefin reactions. The reactions to form higher order polyolefins, such as polyethylenes of varying grades, are dependent on the comonomer introduced into the reaction. As the demand for polyethylenes that incorporate one or more comonomer, the demand for 1-hexene and other select comonomers also increases. The trimerization reaction of ethylene to 1-hexene represents one method of manufacturing desired oligomer product as needed. Similarly, 1-octene and other desired oligomer products can be produced in high selectivity via ethylene oligomerization using homogeneous chromium catalyst systems activated by an appropriate aluminum compound. Such selective oligomerization reactions have been performed for many years with many optimization efforts. Exemplary past processes descriptive of the reaction chemistry can be found at least in U.S. Pat. No. 7,157,612, and in International Patent Publication Nos. WO2007/092136 and WO2009/060343, each of which is incorporated herein by reference in its entirety for all purposes. One of the major challenges associated with the selective oligomerization of ethylene (or other olefins) is the control of the reaction to maximize production rates while maintaining selectivity to the desired oligomer and maximizing catalyst utilization rates.

One part of controlling these chemical processes is the step of quenching the catalyst. Typically quenching can be achieved by introducing a component that converts the catalyst composition to a composition that can no longer promote the reaction of the feed components. Such components are sometimes referred to as "catalyst-deactivating compositions." The amount of catalyst-deactivating composition necessary to completely deactivate the catalyst composition can be calculated from the chemical equation of the deactivation reaction. But due to a number of factors (e.g., insufficient mixing), incomplete deactivation can occur even in the presence of sufficient amounts of the catalyst-deactivating composition. Problems associated with incomplete mixing can be aggravated when the reaction product mixture includes more than one liquid phase because the catalyst and the catalyst-deactivating composition may partition at different concentrations in the two phases, thereby creating a relative depletion of catalyst-deactivating composition in the phase to which the catalyst migrates despite the presence of sufficient quantities of catalyst-deactivating composition in the overall mixture. In other processes, the catalyst composition can migrate from solution to the vapor phase as the solvent evaporates. The presence of the catalyst in the vapor phase allows for further reactions creating unwanted by-products (e.g., aluminum-containing precipitates) that may clog piping or lead to processing problems.

There is therefore a need for a method of deactivating a catalyst that avoids problems associated with incomplete mixing and downstream catalytic activity leading to processing problems. Such a method would be particularly useful in an oligomerization process since oligomerization processes often produce multiphase product streams whereby the oligomers are separated by volatilization.

SUMMARY

In one aspect, embodiments of the invention provide a method of deactivating a catalyst comprising providing to a product-receiving vessel i) a reaction product stream comprising a catalyst composition and at least one product composition; ii) a catalyst-deactivating composition having a boiling point, b.p.(cdc); and iii) a diluent having a boiling point, b.p.(dil), wherein b.p.(dil)≥b.p.(cdc)+5.0° C.; and contacting in a vapor phase of the product-receiving vessel at least a portion of the catalyst composition with at least a portion of the catalyst-deactivating composition. Preferably, the equivalent ratio of catalyst-deactivating composition to catalyst composition in the reaction product stream is from 0.10:1 to 0.70:1. Preferably, the method further includes removing at least a portion of the reaction product from an upper portion of the product-receiving vessel; and removing at least a portion of the diluent from a lower portion of the product-receiving vessel.

In another aspect, embodiments of the invention provide a method of deactivating a catalyst comprising directing a reaction product stream comprising a catalyst composition and at least one reaction product to a product-receiving vessel; providing a catalyst-deactivating composition having a boiling point, b.p.(cdc) and a diluent having a boiling point, b.p.(dil), to the product-receiving vessel; wherein b.p.(dil)≥125.0° C. b.p.(cdc)≤105.0° C., and contacting in a vapor phase of the product-receiving vessel at least a portion of the catalyst composition with at least a portion of the catalyst-deactivating composition.

Embodiments of the invention also provide a method of producing oligomers of olefins, the method comprising initiating an olefin oligomerization reaction with a first amount of catalyst composition in a reaction system to produce an oligomerization product; transferring the oligomerization product and a diluent to a product-receiving vessel; separating the oligomerization product and a second amount of the catalyst composition from the diluent; and deactivating the second amount of the catalyst composition in the product receiving vessel with an amount of a catalyst-deactivating composition, wherein the amount of the catalyst-deactivating composition is less than a stoichiometric amount necessary to deactivate the first amount of the catalyst composition. Preferably, the substoichiometric amount is an equivalent ratio of catalyst-deactivating composition to catalyst composition in the reaction product stream is from 0.10:1 to 0.70:1.

In still another aspect, embodiments of the invention provide an oligomerization system for preparing oligomers from monomers, the oligomerization system comprising: a) an oligomer synthesis reactor, adapted to receive at least one monomer, a catalyst composition, and a reaction medium, and adapted to convert the at least one monomer to an oligomer product composition; b) a catalyst deactivation system for delivering a catalyst-deactivating composition and a diluent to a reactor product stream of the oligomerization synthesis reactor, the reactor product stream comprising oligomer product, and at least a portion of the catalyst composition, the catalyst-deactivating composition, and the diluent, wherein the equivalent ratio of catalyst-deactivating composition to catalyst composition in the reaction product stream is from 0.10:1 to 0.70:1; c) a gas/liquid phase separation system adapted to receive the reactor product stream and to form a first recycle stream and a separation system product stream; wherein the first recycle stream and the separation system product stream are essentially free of the catalyst composition; and d) a recycle loop adapted to recycle the first recycle stream to the oligomer synthesis reactor, wherein the first recycle stream comprises reaction medium and unreacted monomer, wherein the separator product stream comprises a majority portion of the oligomer product in the gas phase effluent, and wherein at least a portion of the separation system product stream is utilized as the oligomer product stream.

DETAILED DESCRIPTION

The invention is directed to methods of deactivating a catalyst, preferably where the catalyst is combined with a product-containing vapor phase. In the methods herein, careful selection of the catalyst-deactivating composition and a relatively higher boiling diluent preferentially segregates the deactivating composition to a vapor phase in a post-reactor gas/liquid separation step. Small amounts of catalyst composition that typically migrate to the product and/or recycle stream in the vapor phase can be prevented from negatively impacting the recycle stream and downstream product processing using a surprisingly small amount of deactivating agent.

While such methods are described herein with respect to deactivation of a catalyst in an oligomerization process, one of ordinary skill in the art will recognize that such process can be broadly applied to other processes. In an effort to provide a concise description of the embodiments of the invention, not all features of an actual implementation are described in the specification. It should be appreciated that in the development of any such actual implementation, as in any engineering or design project, numerous implementation-specific decisions must be made to specific design targets, e.g., compliance with system-related and business-related constraints. Moreover, it should be appreciated that such a development effort might be complex and time consuming, but would nevertheless be a routine undertaking of design, fabrication, and manufacture for those of ordinary skill having the benefit of this disclosure. Accordingly, the equipment and processes illustrated in the Figures are intentionally generic due to the many implementation-specific variables that will affect the individual component equipment parts and illustrate the relationship between the parts rather than the nuances of the specific parts.

For any particular compound disclosed herein, the general structure or general name presented is intended to encompass all structural isomers, conformational isomers, and stereoisomers that may arise from a particular set of substituents, unless indicated otherwise. Thus, a general reference to a compound includes all structural isomers unless explicitly indicated otherwise, e.g., a general reference to pentane includes n-pentane, 2-methyl-butane, and 2,2-dimethylpropane.

Figure 1:
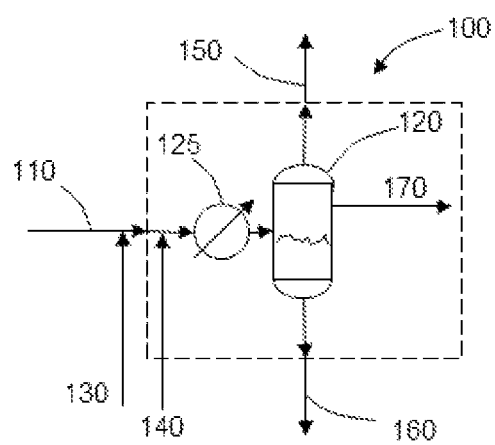
FIG. 1 schematically illustrates a catalyst deactivation system useful in embodiments of the invention.

FIG. 1 shows a schematic representation of a catalyst deactivation system 100 wherein reaction product stream 110 from a reactor such as an oligomerization reactor, the product stream 110 comprising a catalyst composition, at least one product composition and typically a reaction medium is provided to a product-receiving vessel 120, (e.g., a flash vessel, fractionation column, etc.) through an optional heat exchanger 125. Stream 130 provides a catalyst-deactivating composition to the reaction product stream 110 to deactivate the catalyst composition to reduce or minimize the formation of undesirable compounds (e.g., isomers, other contaminants, etc.) in downstream processing systems. A diluent stream 140 provides diluent to the reaction product stream 110 as depicted in FIG. 1. In other embodiments, the diluent stream 140 provides diluent to the product-receiving vessel 120. The order of addition of the catalyst-deactivating composition and the diluent to the product stream is not critical. Likewise, while FIG. 1 depicts streams 130 and 140 entering the product stream 110 prior to the optional heat exchanger 135, other embodiments envision streams 130 and 140 entering the product stream 110 after the optional heat exchanger.

In a preferred embodiment of the invention, the product-receiving vessel 120 separates light components into a light component vapor phase stream 150 (e.g., unreacted olefins and optionally product), and heavy liquid components into a heavy component liquid stream 160 (e.g., diluent, reaction by-products, optionally at least some of the reaction medium if present, etc.). In a preferred configuration, the catalyst deactivation system 100 is configured so that the light component vapor stream 150 removes unreacted olefins and oligomerized products via an overhead stream exiting the reaction-product vessel. Alternatively, the light components and products are removed from separate vapor streams. For example, the product may exit product-receiving vessel from a side draw 170 while lighter components exit an overhead light component stream 150 and the heavy component liquid stream 160 exits as a bottoms stream. As appreciated by one of ordinary skill in the art, light components generally refer to components having a higher vapor pressure and/or lower boiling point than the diluent, and heavy components generally refer to components having a lower vapor pressure and/or higher boiling point than the product or diluent. Whatever configuration is employed for removal of the product, the product-containing stream exiting the product-receiving vessel 120 is generally further processed (not depicted) in order to isolate the product from other components, including recycling the diluent and/or reaction medium for re-use in the upstream oligomerization reactor. Preferably, additional catalyst-deactivating composition, which may be the same or different composition from that added to the reaction product stream 110, is added to the heavy component liquid stream 160 downstream from the product-receiving vessel 120.

The light component vapor stream 150 may include ethylene and reaction co-products, such as hydrocarbon compounds having less than about 5 carbon atoms per molecule. The light component vapor stream 150 may include other non-hydrocarbon compounds such as hydrogen, nitrogen, oxygen, carbon monoxide, carbon dioxide, and water. The product/diluent side draw 170 generally includes compounds having similar boiling points, for example, compounds having similar numbers of carbons. In an embodiment, the product/diluent side draw 170 contains the $C_6$ compounds product 1-hexene and diluent cyclohexane. The heavy component liquid stream 160 may include hydrocarbon compounds having from about 7 to about 100 carbon atoms per molecule and may also include higher olefinic products, such as, for example decenes and tetradecenes, as well as polymeric products, catalyst composition residues, and deactivated catalyst composition.

Figure 2:
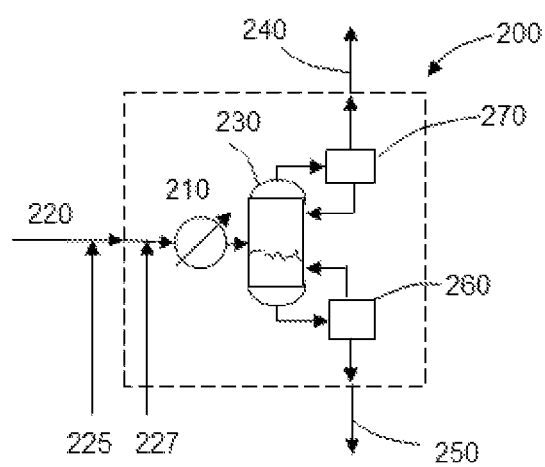
FIG. 2 schematically illustrates a catalyst deactivation system useful in embodiments of the invention.

FIG. 2 illustrates an embodiment of a catalyst deactivation system 200 includes a distillation system. The catalyst deactivation system 200 includes a heat exchanger 210 to control the temperature of the reactor product stream 220 to the distillation tower 230. As described with respect to stream 130 in FIG. 1, stream 225 provides a catalyst-deactivating composition, and a diluent stream 227 provides diluent to the reaction product stream 220 as depicted in FIG. 2. Alternatively, the diluent stream 227 provides diluent to the distillation tower 230. The order of addition of the catalyst-deactivating composition and the diluent to the product stream is not critical. Streams 225 and 227 may enter the product stream 220 prior to, or after the optional heat exchanger 210. The distillation tower 230 and its preparatory heat exchanger 210 may be configured based on factors such as the properties of the reactor product stream 220 and the desired compositions and properties of the first recycle stream 240 which may also include light components such as ethylene, reaction co-products, (e.g., hydrocarbon compounds having fewer than about 5 carbon atoms per molecule), hydrogen, nitrogen, oxygen, carbon monoxide, carbon dioxide, water, etc. As illustrated, the distillation system 200 of FIG. 2 includes a reboiler apparatus 260, and a reflux apparatus 270, which may be implemented according to conventional distillation system technologies. Implementations of the present systems and methods may select systems according to FIG. 1, FIG. 2, or any other suitable gas/liquid phase separation system.

Oligomerization Process

Figure 3:
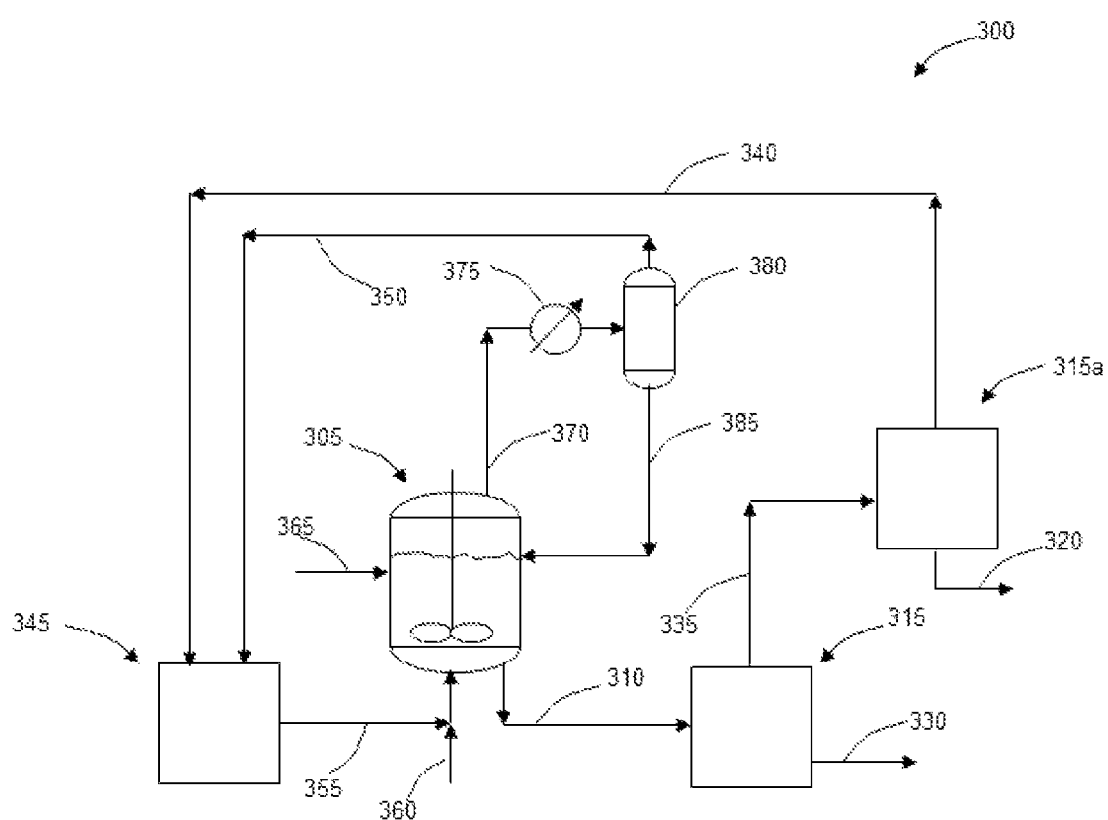
FIG. 3 schematically illustrates an oligomerization process employing the catalyst deactivation system useful in embodiments of the invention.

Catalyst deactivation systems can be incorporated into a variety of reaction systems. One such system is an oligomerization system 300, schematically illustrated in FIG. 3, which includes reactor 305. While FIG. 3 depicts a generic reactor, the skilled person will recognize that different types of reactors, including a solution reactor, a continuous stirred tank, a slurry reactor, a loop reactor, or a gas phase reactor, could also be used with the catalyst deactivation systems and methods described herein. Furthermore, more than one reactor may be used, with the reactors being in sequence, in parallel, or in combinations thereof. In one embodiment, as discussed herein, a loop reactor may be used. In the loop reactor, the catalyst composition and any insoluble reactants or products may be suspended by agitation in a circulated loop. The desired oligomer product is withdrawn from the reactor 305 as a liquid mixture, including the desired oligomer, catalyst, reaction solvent, and still unreacted monomer.

Whatever reactor design is employed, one product will typically be a liquid mixture such as a conventional reactor bottoms stream 310 that may undergo any of several processes, shown generally as process box 315, 315a to isolate a product stream 320. In the illustration of FIG. 3, the first process 315 includes the inventive catalyst deactivation method, particularly as described in FIG. 1 or 2. The first process 315 isolates byproducts and other waste materials in a purge stream 330 and to provide an enriched stream 335. The purge stream 330 may include components such as used catalyst and reaction by-products, like longer chain polymers. The enriched stream 335 illustrated in FIG. 3 conventionally comprises the desired oligomer, unreacted monomer, and reaction medium. Continuing with the description of the representative oligomer synthesis reactor system 300 of FIG. 3, the enriched stream 335 is then passed through a second process 315a to further separate the desired oligomer from the reaction solvent and the unreacted monomer. As illustrated, second process 315a produces a recycle stream 340 and the product stream 320. The recycle stream 340 generally comprises reaction solvent and unreacted monomer, with preferably very little of the desired oligomer.

FIG. 3 illustrates further aspects of an oligomer synthesis reactor system 300. As can be seen, the reaction medium recycle stream 340 is directed to a mixer 345 and combined with a vapor recycle stream 350. The mixer 345 may include a cooler or other heat exchange facility to change the properties of the combined recycle stream 355. The combined recycle stream, a monomer make-up stream 360, and a catalyst feed 365 are each illustrated as inputs to the reactor 305. Additionally, the reactor system 300 is provided with evaporative cooling features, including a reflux of condensed portions of the gaseous reactor top stream 370. As is well understood, the oligomerization reaction is exothermic and temperature control is a critical aspect of successful operations. Evaporative cooling operations remove heat from the reaction by allowing a portion of the reaction solution to evaporate. As suggested previously, the inputs to the reactor, such as the combined recycle stream 355 may be temperature controlled to further regulate the temperature inside the reactor 305. In the illustration of FIG. 3, and as previously disclosed in WO2007/092136, reactor systems 300 including evaporative cooling features may include a chiller 375 and a separator 380 to provide a liquid separator bottoms stream 385 and the vapor recycle stream 350. While the separator will not necessarily completely separate the heavy and light components in the overhead stream 370, the heavier components will be more concentrated in the separator bottoms stream 385 and the lighter components will be more concentrated in the separator vapor recycle stream 350.

Figure 4:
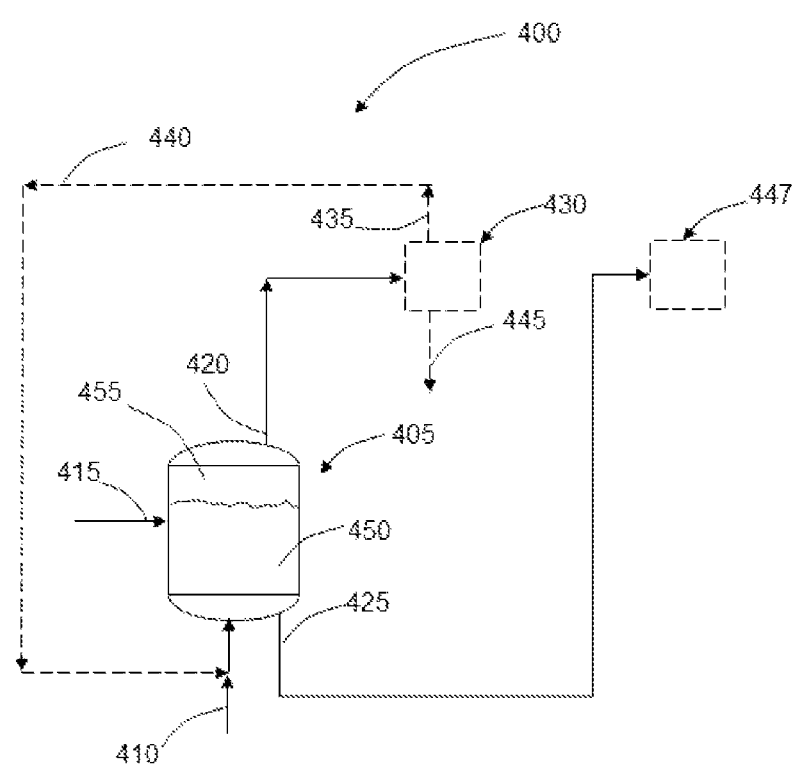
FIG. 4 schematically illustrates an oligomerization process employing the catalyst deactivation system useful in embodiments of the invention.

FIG. 4 provides another representative schematic of an oligomerization system suitable for use with the method of deactivating a catalyst. The oligomerization system 400, which includes an oligomer synthesis reactor 405 a monomer feed stream 410 and a catalyst feed stream 415. FIG. 4 further illustrates a vapor phase effluent 420 and a liquid phase effluent 425 exiting the reactor 405. As illustrated, the vapor phase effluent 420 is directed to the gas/liquid phase separation system 430. Where system 400 is designed in a manner such vapor phase effluent 420 includes the desired product, the gas/liquid phase separation system 430 can include or consist of the inventive catalyst deactivation system. Whatever gas/liquid phase separation system 430 is used it will provide a first recycle stream 435. The first recycle stream 435 may be recycled through a recycle loop 440 to the oligomer synthesis reactor 405. While the recycle loop 440 is illustrated as a simple recycle line, it should be understood the various conventional processes may be implemented on the recycle loop 440, such as mixing, heat exchange, compression, etc., before directing the first recycle stream back to the reactor 405. In oligomerization systems 400 where the vapor phase effluent 420 includes the desired product, the gas/liquid phase separation system 430 also provides a separator product stream 445 that includes the desired product. In other embodiments, the system 400 may be designed so that the liquid phase effluent 425 from the reactor 405 includes the desired product. In such cases, the liquid phase effluent 425 can be directed to a separation process 447 that includes or consists of the inventive catalyst deactivation system, including the various input and output streams described above in FIGS. 1 and 2 as may be appropriate for particular oligomerization system 400 design elements.

With the primary components of the oligomerization system 400 described, specifics of certain components will now be described for clarity. The oligomer synthesis reactor 405 may be any suitable reactor configuration, which may be selected based on factors such as catalyst systems and monomers being used and oligomer product being produced. Preferably, the reactor 405 is adapted to include a liquid phase region 450 and a vapor phase region 455. As can be expected, the vapor phase region 455, is above the liquid phase region 450. The feed streams to the reactor 405, such as the monomer feed stream 410, the catalyst feed stream 415, and the first recycle stream 435, enter the reactor in the liquid phase region 450, regardless of the state of the materials in the stream. The oligomerization reaction occurring inside the reactor 405 generates heat (i.e., the reaction is exothermic). Accordingly, compositions in the reactor in the liquid phase, and having a boiling point below the internal temperature of the reactor, will be evaporated, and flow into the vapor phase region 455.

As has been described in prior patent applications, which have been incorporated herein by reference above, the reaction conditions in the reactor 405 may be controlled to maintain a desired temperature range within the reactor 405 by evaporative cooling. For example, the evaporation of the liquid phase and evacuation of the resultant vapor phase, or portions thereof, may withdraw sufficient energy of vaporization from the reactor to maintain a desired temperature. One exemplary implementation may maintain a desired temperature range by introducing excess monomer in order to maintain a specific rate of evaporation. For example, the reaction temperature may be maintained between about 50° C. and about 150° C. while maintaining the reaction pressure between about 150 psi (10.5 kg/cm$^2$) to about 900 psi (63.3 kg/cm$^2$). Additionally or alternatively, the temperature and/or the pressure may be controlled or regulated by other means, such as through the use of cooling equipment or pressurization equipment, within the reactor and/or on one or more of the feed streams. Reaction conditions selected to provide evaporative cooling with concurrent condensation on walls of the reactor 405 or other equipment has been found to provide anti-fouling benefits. Exemplary processes that may incorporate the catalyst deactivation system described herein can be found at least in U.S. Pat. No. 7,157,612, and in International Patent Publication Nos. WO2007/092136 and WO2009/060343, each of which is incorporated herein by reference in its entirety for all purposes. Other oligomerization processes suitable for use with the methods and apparatuses described herein are disclosed in U.S. Provisional Application No. 61/489,424 filed May 24, 2011, incorporated by reference herein in its entirety.

Monomer Feedstocks

Monomer feedstocks comprise one or more oligomerizable olefinic compounds such as $C_2$ to $C_{30}$, preferably $C_2$ to $C_{16}$, or more preferably $C_2$ to $C_{10}$ olefinic compounds. Preferred olefinic compounds include alpha-olefins, such as ethylene, propylene, 1-butene, 1-hexene, 1-octene, and 1-decene, particularly ethylene, and propylene, most particularly ethylene.

Catalyst Compositions

Any composition suitable for catalyzing the oligomerization of olefins may be used in the methods described herein. Preferred product of the oligomerization process such as 1-hexene, 1-octene, and other desired oligomers can be produced in high selectivity via ethylene trimerization using homogeneous, single-site catalyst systems, preferably a chromium-containing single-site catalyst, activated by a molar excess of alkyl aluminums such as methyl alumoxane (MAO) and modified methyl alumoxane (MMAO). Some such catalysts may be formed from a metal precursor as is known in the art. Chromium compounds that may be used as the metal precursor include organic or inorganic compounds in which the chromium oxidation state is from 0 to 6. Generally, the chromium source will have a formula of $CrX_n$, in which each X can be the same or different and may be any organic or inorganic radical, and n may be an integer from 1 to 6. Organic radicals that may be used for X, may have from about 1 to about 20 carbon atoms per radical, and may include alkyl, alkoxy, ester, ketone, carboxylate, or amido radicals, among others. The organic radicals may be straight-chained or branched, cyclic or acyclic, aromatic or aliphatic, and may include mixed aliphatic, aromatic, or cycloaliphatic groups. Exemplary inorganic radicals include, but are not limited to, any anion or oxidizing radical, for example, halides, sulfates, or oxides. Exemplary metal precursor include, but are not limited to, chromium compounds, such as organometallic chromium (II) or chromium (III) compounds, or a mixture thereof.

The organometallic chromium compounds which may be used as the metal source for the oligomerization catalyst composition may be a chromium(II) carboxylate or a chromium(III) carboxylate; alternatively, a chromium(II) carboxylate; or alternatively, a chromium(III) carboxylate. Each carboxylate of the chromium(II) or chromium(III) carboxylate may be a $C_1$ to $C_{20}$, a $C_3$ to $C_{15}$, or a $C_4$ to $C_{10}$ carboxylate. Examples of oligomerization catalyst compositions, and their exemplary preparation and use are described in U.S. Pat. Nos. 6,133,495; 7,994,086; 7,384,886, 7,384,886, and 8,049,052, each of which are incorporated herein by reference in its entirety.

Reaction Solvent

If employed, any number of aliphatic or aromatic liquid may be used as a reaction medium for the oligomerization reactions described herein. Generally, the reaction medium will be stable with respect to the oligomerization process, e.g., having no functional group (e.g. double bonds) that undesirably react under oligomerization conditions. In some embodiments, an excess of one or more alpha-olefins, e.g. a monomer, serves as the reaction medium. Accordingly, the reaction medium is typically selected from $C_4$ to $C_{24}$, preferably $C_4$ to $C_{15}$, more preferably $C_4$ to $C_{10}$ aliphatic compounds. Exemplary aliphatic compounds include, but are not limited to 1-butene, 1-hexene, 1-octene, toluene, propane, butane, isobutane, pentane, isopentane, hexane, heptane, and combinations thereof. The choice of the reaction medium may be made on the basis of convenience in processing. For example, isobutane may be chosen to be compatible with the reaction medium used for the formation of polyolefins in a subsequent processing step. Since 1-hexene may be the reaction product of the oligomerization, it may be chosen as the reaction medium to decrease the need for separation. Further, cyclohexane or methylcyclohexane may be chosen to solubilize the products made during the oligomerization. In a preferred embodiment, the reaction medium is hexane.

Catalyst-Deactivating Composition

A feature of the methods described herein is that the amount the catalyst-deactivating composition provided to the reaction product stream is less than stoichiometrically required to deactivate the amount of catalyst in the product stream. In other words, in the inventive methods, the number of equivalents of the catalyst-deactivating composition is less than required by the deactivation reaction of the deactivating composition with the catalyst. The equivalent ratio of catalyst-deactivating composition to catalyst may be in the range of from greater than 0:1.0 to less than 1:1. In preferred embodiments, the lower limit on the range of the equivalent ratio may be 0.01:1, 0.02:1, 0.03:1, 0.05:1, 0.075:1, 0.10:1, 0.20:1, 0.30:1, 0.40:1, 0.50:1, 0.60:1, or 0.70:1. Preferred upper limits on the range of the equivalent ratio may be 0.70:1, 0.60:1, 0.50:1, 0.40:1, 0.30:1, 0.20:1, 0.10:1, 0.075:1, 0.05:1, 0.03:1, 0.02:1, or 0.01:1. While certain preferred ranges include those where any lower limit and upper limit may be used, preferred embodiments have a range of the equivalent ratio of catalyst-deactivating composition to catalyst of 0.10-0.70:1, 0.1-0.60:1, 0.1-0.50:1, 0.1-0.40:1, 0.20-0.70:1, 0.20-0.60:1, 0.20-0.50:1, 0.20-0.40:1, 0.30-0.70:1, 0.30-0.60:1, 0.30-0.50:1, or 0.30-0.40:1. In some preferred embodiments, the ratio is 0.40-0.70:1, 0.40-0.60:1, 0.40-0.50:1, 0.50-0.70:1, or 0.5-0.60:1.

The catalyst-deactivating composition is selected from the group consisting of amines, alcohols, or mixtures thereof. In some embodiments, the catalyst-deactivating composition is selected from the group consisting of mono alcohols, diols, polyols, or mixtures thereof. In some embodiments, the catalyst-deactivating composition is a $C_2$ to $C_{20}$ mono alcohol. In some embodiments, the catalyst-deactivating composition is selected from the group consisting of a ethanol, propanol, butanol, a pentanol, a hexanol, a heptanol, an octanol, and nonanol, a decanol, a undecanol, or mixtures thereof. In some embodiments, the catalyst-deactivating composition is selected from the group consisting of 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-udecanol, 7-methyl-2-decanol, a 1-docecanol, a 2-dodecanol, 2-ethyl-1-decanol, and mixtures thereof. In one embodiment, the catalyst-deactivating composition comprises 2-ethyl-1-hexanol. Water is a preferred catalyst-deactivating composition. Where the catalyst-deactivating composition is a mixture, the boiling point of the catalyst-deactivating composition, b.p. (cdc) is the boiling point of the lowest boiling diluent in the mixture.

Diluent

In the methods of the invention a diluent is added to the reactor product, typically to the reaction product stream. The diluent is selected to have a boiling point at least 5.0° C. greater than the boiling point of the catalyst deactivating composition. In other words b.p.(dil) is ≥b.p.(cdc)+5.0° C. Particular diluents have a boiling point, b.p.(dil) preferably at least 10° C. greater, more preferably at least 15° C. greater, at least 20° C. greater, at least 25° C. greater, or at least 30° C. greater, than the boiling point of the catalyst-deactivating composition, b.p.(cdc). Preferably, the boiling point of the diluent, b.p.(dil), is ≥110.0° C., ≥115.0° C., ≥120.0° C., or ≥125.0° C. and b.p.(cdc)≤105.0° C., ≤100.0° C., ≤95.0° C., ≤90.0° C., or ≤80.0° C.

Generally, the diluent comprises an aliphatic hydrocarbon selected from $C_6$ to $C_{24}$, preferably $C_8$ to $C_{20}$, $C_8$ to $C_{15}$, more preferably $C_8$ to $C_{12}$ aliphatic compounds. If a reaction medium is used, the diluent may be the same or different than the reaction medium. Preferred diluents include octanes, decanes, dodecanes, and mixtures thereof. Where the diluent is a mixture, the boiling point of the diluent, b.p. (dil) used to determine the difference between the boiling point of the diluent and the catalyst-deactivating composition is the boiling point of the highest boiling diluent in the mixture.

In preferred combinations the diluent is a substituted or unsubstituted, linear or branched $C_8$ to $C_{12}$ aliphatic compound, more preferably octane, decane, dodecane, and mixtures thereof, and the catalyst-deactivating composition comprises ethanol, propanol, water, and mixtures thereof. More preferred combinations are those wherein the diluent is octane, decane, or dodecane, and the catalyst-deactivating composition is water. Still more preferred combinations are those wherein the diluent is decane and the catalyst-deactivating composition is water.

Product Composition

The oligomer or product alpha olefin of the present techniques generally comprises less than 75 units derived from monomer(s). Some preferred products comprise 2 to 30, more preferably 2 to about 20, preferably less than about 10, 9, 8, 7, 6, 5, 4, or 3 units derived from monomer(s). For example, preferred products 1-hexene and 1-octene include 3 and 4 units derived from ethylene, respectfully. Likewise, 1,5-cyclooctadiene may be formed from 3 units of 1,3-butadiene. Other olefinic compounds may be reacted with different olefinic compounds to give useful products. For example, the co-trimerization of ethylene and hexene which may result in 1-decene, 1-tetradecene, or a mixture thereof. In other examples, co-trimerization of ethylene and 1-butene may result in octenes, and co-trimerization of 1-decene and ethylene may result in tetradecenes, dodecenes, or a mixture of both. In determining the number of monomer units in a particular product, it should be noted that a single molecule may contain two monomer units. For example, dienes, such as 1,3-butadiene and 1,4-pentadiene, have two monomer units within one molecule.

The processes described herein are capable of providing a product composition containing an oligomerized product composition, wherein the oligomerized product composition comprises at least 70.0 wt. %, preferably 80.0 wt. %, 90.0 wt. %, 95.0 wt. %, 99.0 wt. %, 99.9 wt. %, or greater alpha-olefins having from 2 to 10 units derived from the one or more monomers. Some preferred processes are capable of providing a mixture of oligomerized products containing at least 70.0 wt. %, preferably 80.0 wt. %, 90.0 wt. %, 95.0 wt. %, 99.0 wt. %, 99.9 wt. %, or greater amount of an alpha-olefin comprising 3 units derived from one or more monomers. The alpha-olefin formed in the process described herein, such as 1-hexene, may be used as a co-monomer in a polyolefin polymerization or as a feedstock to other chemical processes.

Embodiments

Accordingly, the present invention provides the following embodiments of the invention.

A. Embodiments of the invention provide a method of deactivating a catalyst comprising: providing to a product-receiving vessel i) a reaction product stream comprising a catalyst composition and at least one product composition; ii) a catalyst-deactivating composition having a boiling point, b.p.(cdc); iii) a diluent having a boiling point, b.p.(dil), wherein b.p.(dil)≥b.p.(cdc)+5.0° C.; and contacting in a vapor phase of the product-receiving vessel at least a portion of the catalyst composition with at least a portion of the catalyst-deactivating composition.

B. Embodiments of the invention include the method of Embodiment A, wherein the method further includes removing at least a portion of the at least one reaction product from an upper portion of the product-receiving vessel; and removing at least a portion of the diluent from a lower portion of the product-receiving vessel.

C. Embodiments of the invention include the methods of any of Embodiments A-B, wherein the equivalent ratio of catalyst-deactivating composition to catalyst composition in the reaction product stream is from 0.01:1 to 0.70:1.

D. Embodiments of the invention include the methods of any of Embodiments A-C, wherein the catalyst-deactivating composition comprises a composition selected from the group consisting of a ethanol, propanol, butanol, a pentanol, a hexanol, a heptanol, an octanol, and nonanol, a decanol, a undecanol, or mixtures thereof.

E. Embodiments of the invention include the methods of any of Embodiments A-D, wherein the catalyst-deactivating composition comprises water.

F. Embodiments of the invention include the methods of any of Embodiments A-E, wherein the reaction product stream further includes a reaction medium selected from the group consisting of 1-butene, 1-hexene, 1-octene, toluene, propane, butane, isobutane, pentane, isopentane, hexane, heptane, and combinations thereof.

G. Embodiments of the invention include the methods of any of Embodiments A-F, wherein catalyst composition includes a chromium-containing single-site catalyst and an alkyl aluminum activator.

H. Embodiments of the invention include the methods of any of Embodiments A-G, wherein the catalyst composition comprises a chromium-containing single site catalyst comprising the reaction product of a chromium(II) carboxylate or a chromium(III) carboxylate, wherein each carboxylate of the chromium(II) or chromium(III) carboxylate may be the same or different and is selected from the group consisting of $C_1$ to $C_{20}$ carboxylates and the alkyl aluminum activator comprises methyl alumoxane (MAO) or modified methyl alumoxane (MMAO).

I. Embodiments of the invention include the methods of any of Embodiments A-H, wherein the diluent comprises an aliphatic hydrocarbon selected from $C_6$ to $C_{24}$ aliphatic compounds.

J. Embodiments of the invention include the methods of any of Embodiments A-I, wherein the diluent comprises a substituted or unsubstituted, linear or branched $C_8$ to $C_{12}$ aliphatic compound.

K. Embodiments of the invention include the methods of any of Embodiments A-J, wherein the diluent comprises octane, decane, dodecane, and mixtures thereof and the catalyst-deactivating composition comprises ethanol, propanol, water, and mixtures thereof.

L. Embodiments of the invention include the methods of any of Embodiments A-K, wherein diluent comprises decane and the catalyst-deactivating composition comprises water.

M. Embodiments of the invention include the methods of any of Embodiments A-L, wherein b.p.(dil), ≥110.0° C. and b.p.(cdc)≤105.0° C., preferably wherein b.p.(dil)≥125.0° C. and b.p.(cdc)≤100.0° C.

N. Embodiments of the invention include the methods of any of Embodiments A-M, wherein b.p.(dil) is preferably at least 10° C. greater, more preferably at least 15° C. greater, at least 20° C. greater, at least 25° C. greater, or at least 30° C. greater, than the boiling point of the catalyst-deactivating composition, b.p.(cdc).

O. Embodiments of the invention include the methods of any of Embodiments A-N, wherein the boiling point of the diluent, b.p.(dil), is ≥110.0° C., ≥115.0° C., ≥120.0° C., or ≥125.0° C. and b.p.(cdc)≤105.0° C., ≤100.0° C., ≤95.0° C., ≤90.0° C., or ≤80.0° C.

P. Embodiments of the invention include the methods of any of Embodiments A-O, wherein the at least one product composition comprises an alpha olefin having less than 75 units derived from one or more monomers.

Q. Embodiments of the invention include the methods of any of Embodiments A-P, wherein the at least one product composition an oligomerized product composition, wherein the oligomerized product composition comprises at least 70.0 wt. % of an alpha-olefin of one or more monomers, the alpha-olefin having from 2 to 10 units derived from the one or more monomers.

R. Embodiments of the invention include the methods of any of Embodiments A-Q, wherein the at least one oligomerized product composition comprises at least 70.0 wt. % of an alpha-olefin comprising 3 units derived from one or more monomers.

S. Embodiments of the invention include the methods of any of Embodiments A-R, wherein the at least one product composition is selected from the group consisting of 1-butene, 1-hexene, 1-octene, 1-decene, and mixtures thereof.

T. Embodiments of the invention include the methods of any of Embodiments A-S, wherein the at least one product composition comprises 1-hexene.

U. Embodiments of the invention include a method of deactivating a catalyst comprising: directing a reaction product stream comprising a catalyst composition and at least one reaction product to a product-receiving vessel; providing a catalyst-deactivating composition having a boiling point b.p.(cdc) and a diluent having a boiling point b.p.(dil), to the product-receiving vessel; wherein b.p.(dil)≥125.0° C. and b.p.(cdc)≤105.0° C., and contacting in a vapor phase of the product-receiving vessel at least a portion of the catalyst composition with at least a portion of the catalyst-deactivating composition.

V. Embodiments of the invention include the method of Embodiment U, wherein the catalyst composition comprises a chromium-containing single-site catalyst and an alkyl aluminum activator, preferably the catalyst composition comprises a chromium-containing single site catalyst comprising the reaction product of a chromium(II) carboxylate or a chromium(III) carboxylate, wherein each carboxylate of the chromium(II) or chromium(III) carboxylate may be the same or different and is selected from the group consisting of $C_1$ to $C_{20}$ carboxylates and the alkyl aluminum activator comprises methyl alumoxane (MAO) or modified methyl alumoxane (MMAO).

W. Embodiments of the invention include the methods of Embodiments U-V, wherein the equivalent ratio of catalyst-deactivating composition to catalyst composition in the reaction product stream is from 0.01:1 to 0.70:1.

X. Embodiments of the invention include the methods of Embodiments U-W, wherein the catalyst-deactivating composition comprises a composition selected from the group consisting of a ethanol, propanol, butanol, a pentanol, a hexanol, a heptanol, an octanol, and nonanol, a decanol, a undecanol, or mixtures thereof.

Y. Embodiments of the invention include the methods of Embodiments U-X, wherein the catalyst-deactivating composition comprises water.

Z. Embodiments of the invention include the methods of any of Embodiments U-Y, wherein the diluent comprises an aliphatic hydrocarbon selected from $C_6$ to $C_{24}$ aliphatic compounds, preferably a substituted or unsubstituted, linear or branched $C_8$ to $C_{12}$ aliphatic compound, more preferably the diluent comprises octane, decane, dodecane, and mixtures thereof, and the catalyst-deactivating composition comprises ethanol, propanol, water, and mixtures thereof.

AA. Embodiments of the invention include the methods of any of Embodiments U-Z, wherein the at least one product composition comprises at least one alpha olefin 75 or fewer units derived from one or more monomers wherein at least 70.0 wt. % of the alpha-olefin comprises oligomers having from 2 to 10 units derived from the one or more monomers, more preferably at least 70.0 wt. % the an alpha-olefin comprises oligomers having 3 units derived from one or more monomers, still more preferably the at least alpha-olefin comprises at least 70.0 wt. % 1-butene, 1-hexene, 1-octene, 1-decene, or mixtures thereof, more preferably the at least one product composition comprises 1-hexene.

AB. Embodiments of the invention include a method of producing oligomers of olefins, comprising initiating an olefin oligomerization reaction with a first amount of catalyst composition in a reaction system to produce an oligomerization product; transferring the oligomerization product and a diluent to a product-receiving vessel; separating the oligomerization product and a second amount of the catalyst composition from the diluent; and deactivating the second amount of the catalyst composition in the product receiving vessel with an amount of a catalyst-deactivating composition, wherein the amount of the catalyst-deactivating composition is less than a stoichiometric amount necessary to deactivate the first amount of the catalyst composition.

AC. Embodiments of the invention include the method of Embodiment AB, wherein separating the oligomerization product and a second amount of the catalyst composition from the diluent includes creating a vapor phase comprising the oligomerization product and the second amount of the catalyst composition wherein a major portion of the diluent remains in a liquid phase.

AD. Embodiments of the invention include the methods of any of Embodiments AB-AC, wherein the diluent comprises an aliphatic hydrocarbon selected from $C_6$ to $C_{24}$ aliphatic compounds, preferably a substituted or unsubstituted, linear or branched $C_8$ to $C_{12}$ aliphatic compound, more preferably the diluent comprises octane, decane, dodecane, and mixtures thereof, and the catalyst-deactivating composition comprises ethanol, propanol, water, and mixtures thereof, preferably the diluent has a boiling point≥5.0° C. higher than the boiling point of the catalyst-deactivating composition, preferably the diluent has a boiling≥125.0° C., and the boiling point of the catalyst-deactivating composition≤105.0° C.

AE. Embodiments of the invention include the methods of any of Embodiments AB-AD, wherein the catalyst composition comprises a chromium-containing single-site catalyst and an alkyl aluminum activator, preferably the catalyst composition comprises a chromium-containing single site catalyst comprising the reaction product of a chromium(II) carboxylate or a chromium(III) carboxylate wherein each carboxylate of the chromium(II) or chromium(III) carboxylate may be the same or different and is selected from the group consisting of $C_1$ to $C_{20}$ carboxylates and the alkyl aluminum activator comprises methyl alumoxane (MAO) or modified methyl alumoxane (MMAO).

AF. Embodiments of the invention include the methods of any of Embodiments AB-AE, wherein the equivalent ratio of catalyst-deactivating composition to catalyst composition in the reaction product stream is from 0.01:1 to 0.70:1.

AG. Embodiments of the invention include the methods of any of Embodiments AB-AF, wherein the catalyst-deactivating composition comprises a composition selected from the group consisting of a ethanol, propanol, butanol, a pentanol, a hexanol, a heptanol, an octanol, and nonanol, a decanol, a undecanol, or mixtures thereof.

AH. Embodiments of the invention include the methods of any of Embodiments AB-AG, wherein the catalyst-deactivating composition comprises water.

AI. Embodiments of the invention include the methods of any of Embodiments AB-AH, wherein the oligomer product comprises an alpha olefin having less than 75 units derived from one or more monomers, preferably the oligomer product comprises at least 70.0 wt. % oligomers of one or more monomers, the oligomers having from 2 to 30, or 2 to 10, units derived from the one or more monomers, more preferably at least 70.0 wt. % of an alpha-olefin comprising 3 units derived from one or more monomers, still more preferably the oligomer product comprises at least 70.0 wt. % 1-butene, 1-hexene, 1-octene, 1-decene, or mixtures thereof, more preferably the oligomer product composition comprises at least 70.0 wt. % 1-hexene.

AJ. Embodiments of the invention provide an oligomerization system for preparing oligomers from monomers, the oligomerization system comprising:

an oligomer synthesis reactor; adapted to receive at least one monomer, a catalyst composition, and a reaction medium; and adapted to convert the at least one monomer to an oligomer product composition;

a catalyst deactivation system for delivering a catalyst-deactivating composition and a diluent to a reactor product stream of the oligomerization synthesis reactor, the reactor product stream comprising the oligomer product composition, and at least a portion of the catalyst composition, the catalyst-deactivating composition, and the diluent, wherein the equivalent ratio of catalyst-deactivating composition to catalyst composition in the reaction product stream is from 0.01:1 to 0.70:1;

a gas/liquid phase separation system adapted to receive the reactor product stream and to form a first recycle stream and a separation system product stream; wherein the first recycle stream and the separation system product stream are essentially free of the catalyst composition; and a recycle loop adapted to recycle the first recycle stream to the oligomer synthesis reactor; wherein the first recycle stream comprises reaction medium and unreacted monomer; wherein the separator product stream comprises a majority portion of the oligomer product in the gas phase effluent; and wherein at least a portion of the separation system product stream is utilized as the oligomer product stream.

AK. Embodiments of the invention include the method of Embodiment AJ, wherein the diluent comprises an aliphatic hydrocarbon selected from $C_6$ to $C_{24}$ aliphatic compounds, preferably a substituted or unsubstituted, linear or branched $C_8$ to $C_{12}$ aliphatic compound, more preferably the diluent comprises octane, decane, dodecane, and mixtures thereof, and the catalyst-deactivating composition comprises ethanol, propanol, water, and mixtures thereof, preferably the diluent has a boiling point≥5.0° C. higher than the boiling point of the catalyst-deactivating composition, preferably the diluent has a boiling≥125.0° C. and the boiling point of the catalyst-deactivating composition≤105.0° C.

AL. Embodiments of the invention include the methods of any of Embodiments AJ-AK, wherein the catalyst composition comprises a chromium-containing single-site catalyst and an alkyl aluminum activator, preferably the catalyst composition comprises a chromium-containing single site catalyst comprising the reaction product of a chromium(II) carboxylate or a chromium(III) carboxylate wherein each carboxylate of the chromium(II) or chromium(III) carboxylate may be the same or different and is selected from the group consisting of $C_1$ to $C_{20}$ carboxylates, and the alkyl aluminum activator comprises methyl alumoxane (MAO) or modified methyl alumoxane (MMAO).

AM. Embodiments of the invention include the methods of any of Embodiments AJ-AL, wherein the equivalent ratio of catalyst-deactivating composition to catalyst composition in the reaction product stream is from 0.01:1 to 0.70:1.

AN. Embodiments of the invention include the methods of any of Embodiments AJ-AM, wherein the catalyst-deactivating composition comprises a composition selected from the group consisting of a ethanol, propanol, butanol, a pentanol, a hexanol, a heptanol, an octanol, and nonanol, a decanol, a undecanol, or mixtures thereof.

AO. Embodiments of the invention include the methods of any of Embodiments AJ-AN, wherein the catalyst-deactivating composition comprises water.

AP. Embodiments of the invention include the methods of any of Embodiments AJ-AO, wherein the oligomer product comprises an alpha olefin having less than 75 units derived from one or more monomers, preferably the oligomer product comprises at least 70.0 wt. % oligomers of one or more monomers, the oligomers having from 2 to 30, or 2 to 10, units derived from the one or more monomers, more preferably at least 70.0 wt. % of an alpha-olefin comprising 3 units derived from one or more monomers, still more preferably the oligomer product comprises at least 70.0 wt. % 1-butene, 1-hexene, 1-octene, 1-decene, or mixtures thereof, more preferably the oligomer product comprises at least 70.0 wt. % 1-hexene.

EXAMPLES

Figure 5:
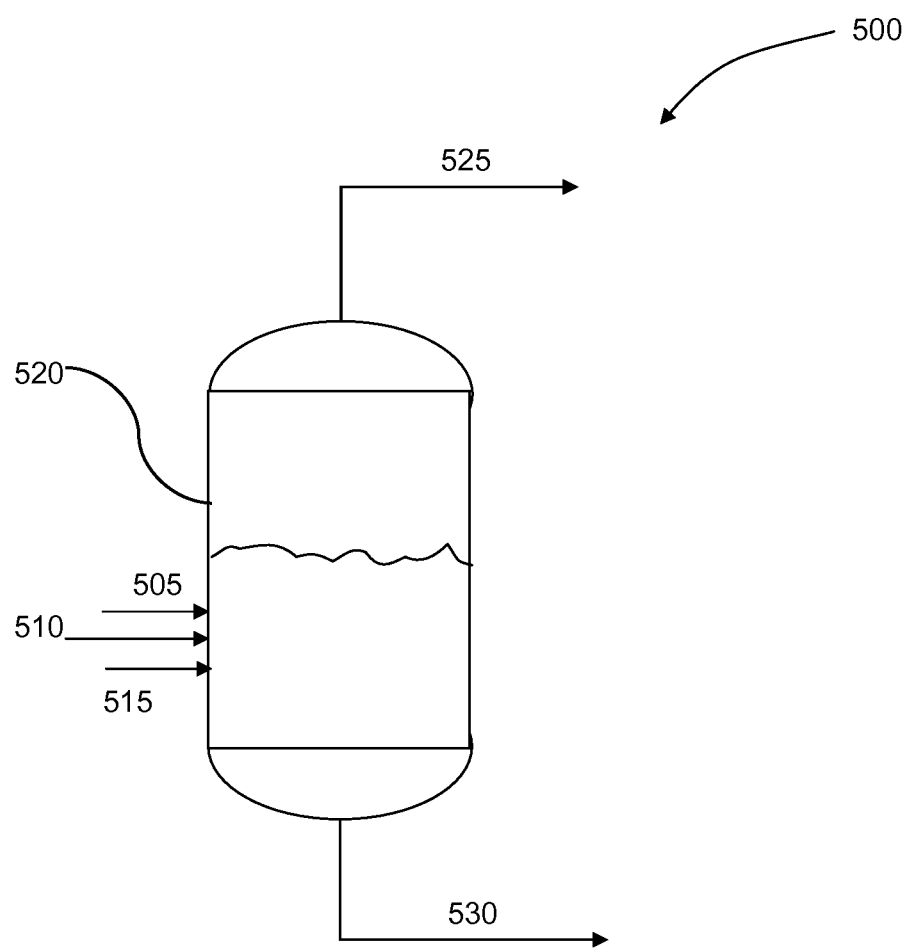
FIG. 5 schematically illustrates experimental design according to an embodiment of the invention.

In a simulation, oligomerization reactor product stream 505 comprising ethylene, hexene, octene, and the reaction medium hexane, a catalyst deactivating composition stream 510 comprising water, and diluent stream 515 are provided to a flash vessel 520 having an overhead flash vapor stream 525 to remove vapor products and a flash liquid stream 530 to remove liquid products. Simulation flow diagram is depicted in FIG. 5. Results of the simulation are shown in Table 1.

| | Reactor Product Stream (Stream 505) | Catalyst-deactivating Composition (Stream 510) | Diluent (Stream 515) | Flash Vapor (Stream 525) | Flash Liquid (Stream 530) |
|---|---|---|---|---|---|
| Temperature (° C.) | 148.9 | 23.9 | 176.7 | 176.7 | 176.7 |
| Pressure (PSIA) | 500 | 14 | 55 | 70 | 70 |
| Total Mass Rate (lb/hr) | 1647 | 18 | 14228 | 1877 | 14017 |
| Stream Phase | Mixed | Water | Liquid | Vapor | Liquid |
| Stream Total Molar Composition Fractions | | | | | |
| Ethylene | 0.625 | 0.000 | 0.000 | 0.597 | 0.021 |
| Water | 0.000 | 1.000 | 0.000 | 0.030 | 0.001 |
| Octene-1 | 0.063 | 0.000 | 0.000 | 0.013 | 0.016 |
| Hexene-1 | 0.313 | 0.000 | 0.000 | 0.129 | 0.060 |
| Decane | 0.000 | 0.000 | 1.000 | 0.231 | 0.903 |
| Methanol | 0.000 | 0.000 | 0.000 | 0.000 | 0.000 |
| Stream Properties | | | | | |
| Total Actual Density (g/cm$^3$) | $7.45 \times 10^{-2}$ | 0.9965 | 0.6015 | $8.5 \times 10^{-3}$ | 0.5944 |
| Vapor Viscosity (cPoise) | 0.01 | n/a | n/a | 0.01 | n/a |
| Liquid Viscosity (cPoise) | 0.10 | 0.91 | 0.20 | n/a | 0.19 |
| Total Molecular Weight (g/mol) | 51.5 | 18.0 | 142.3 | 62.7 | 136.0 |

Table 1 shows that the molar ratio of water in the vapor phase of flash stream 525 is about 30 times greater than in the flash liquid stream 530, meaning the amount of catalyst-deactivating composition needed to deactivate the residual catalyst carried into the product-containing flash stream 525 is much smaller than would be expected according to a 1:1 stoichiometric ratio for the deactivation of the catalyst composition by the deactivating composition. In other words, small amounts of catalyst composition that migrate to the product stream in the vapor phase can be prevented from negatively impacting the downstream product processing and recycle stream by providing a surprisingly small amount of deactivating agent. Active catalyst composition remaining in the flash liquid stream 530 exiting the flash drum can be treated with additional catalyst-deactivating composition, if desired.

The methods described herein to deactivate the catalyst composition may be used with a number of chemical processes. For example, while deactivation of oligomerization reactions and catalyst compositions are described in detail, reactors for other types of chemical products may benefit from the deactivation of at least a portion of the catalyst composition in the vapor phase using a substoichiometric amount of a catalyst-deactivating composition, as discussed herein. Such processes are considered to be within the scope of the invention. Exemplary oligomerization processes, such as exemplary trimerization processes, are described in U.S. Pat. No. 7,384,886; U.S. Publications 2002/0182124; 2004/0236163; and 2005/0197521, all four of which are incorporated herein by reference in their entirety.

Any range of numbers recited in the specification hereinabove, or in the claims hereinafter, such as that representing a particular set of properties, units of measure, conditions, physical states or percentages, is intended to literally incorporate expressly herein by reference or otherwise, any number falling within such range, including any subset of numbers or ranges subsumed within any range so recited.

All documents referred to above are incorporated by reference herein in their entirety unless stated otherwise, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. In some embodiments, the composition is substantially free (i.e., present only at impurity levels or not purposely added to a described composition) of any additive or component other component not specifically enumerated herein. Advantages described for certain embodiments may or may not be present in other embodiments. Likewise, the term "comprising" is considered synonymous with the term "including" for purposes of Australian law. Likewise, whenever a composition, an element, or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

The invention claimed is:

1. A method of deactivating a catalyst comprising:
providing to a product-receiving vessel
  i) a reaction product stream comprising a catalyst composition, and at least one product composition;
  ii) a catalyst-deactivating composition having a boiling point, b.p.(cdc); and
  iii) a diluent having a boiling point, b.p.(dil), wherein b.p.(dil)≥b.p.(cdc)+5.0° C.; and
contacting in a vapor phase of the product-receiving vessel at least a portion of the catalyst composition with at least a portion of the catalyst-deactivating composition; wherein the equivalent ratio of catalyst-deactivating composition to catalyst composition in the reaction product stream is from 0.01:1 to 0.70:1.

2. The method of claim 1, further including removing at least a portion of the at least one reaction product from an upper portion of the product-receiving vessel; and removing at least a portion of the diluent from a lower portion of the product-receiving vessel.

3. The method of claim 1, wherein the catalyst-deactivating composition comprises a composition selected from the group consisting of a ethanol, propanol, butanol, a pentanol, a hexanol, a heptanol, an octanol, and nonanol, a decanol, a undecanol, or mixtures thereof.

4. The method of claim 1, wherein the catalyst-deactivating composition comprises water.

5. The method of claim 1, wherein the reaction product stream further includes a reaction medium selected from the group consisting of 1-butene, 1-hexene, 1-octene, toluene, propane, butane, isobutane, pentane, isopentane, hexane, heptane, and combinations thereof.

6. The method of claim 1, wherein catalyst composition includes a chromium-containing single-site catalyst, and an alkyl aluminum activator.

7. The method claim 1, wherein the catalyst composition comprises a chromium-containing single site catalyst comprising the reaction product of a chromium(II) carboxylate or a chromium(III) carboxylate wherein each carboxylate of the chromium(II) or chromium(III) carboxylate may be the same or different and is selected from the group consisting of $C_1$ to $C_{20}$ carboxylates and the alkyl aluminum activator comprises methyl alumoxane (MAO) or modified methyl alumoxane (MMAO).

8. The method of claim 1, wherein the diluent comprises an aliphatic hydrocarbon selected from $C_6$ to $C_{24}$ aliphatic compounds.

9. The method of claim 1, wherein the diluent comprises a substituted or unsubstituted, linear or branched $C_8$ to $C_{12}$ aliphatic compound.

10. The method of claim 1, wherein the diluent comprises octane, decane, dodecane, and mixtures thereof and the catalyst-deactivating composition comprises ethanol, propanol, water, and mixtures thereof.

11. The method of claim 1, wherein diluent comprises decane and the catalyst-deactivating composition comprises water.

12. The method of claim 1, wherein b.p.(dil), ≥110.0° C. and b.p.(cdc)≤105.0° C.

13. The method of claim 1, wherein b.p.(dil)≥125.0° C. and b.p.(cdc)≤100.0° C.

14. The method of claim 1, wherein the at least one product composition comprises an alpha olefin having less than 75 units derived from one or more monomers.

15. The method of claim 1, wherein the at least one product composition comprises an oligomerized product composition, and at least 70.0 wt. % of the oligomerized product composition comprises alpha-olefins having from 2 to 10 units derived from the one or more monomers.

16. The method of claim 1, wherein the at least one product composition comprises an oligomerized product composition, and at least 70.0 wt. % of the oligomerized product composition comprises an alpha-olefin comprising 3 units derived from one or more monomers.

17. The method of claim 1, wherein the at least one product composition is selected from the group consisting of 1-butene, 1-hexene, 1-octene, 1-decene, and mixtures thereof.

18. The method of claim 1, wherein the at least one product composition comprises 1-hexene.

19. A method of deactivating a catalyst comprising:
directing a reaction product stream comprising a catalyst composition and at least one reaction product to a product-receiving vessel;

providing a catalyst-deactivating composition having a boiling point, b.p.(cdc), and a diluent having a boiling point, b.p.(dil), to the product-receiving vessel; wherein b.p.(dil)≥125.0° C., and b.p.(cdc)≤105.0° C.; and contacting in a vapor phase of the product-receiving vessel at least a portion of the catalyst composition with at least a portion of the catalyst-deactivating composition; wherein the equivalent ratio of catalyst-deactivating composition to catalyst composition in the reaction product stream is from 0.01:1 to 0.70:1.

20. An oligomerization system for preparing oligomers from monomers, the oligomerization system comprising:

an oligomer synthesis reactor; adapted to receive at least one monomer, a catalyst composition, and a reaction medium; and adapted to convert the at least one monomer to an oligomer product composition;

a catalyst deactivation system for delivering a catalyst-deactivating composition and a diluent to a reactor product stream of the oligomerization synthesis reactor, the reactor product stream comprising oligomer product, and at least a portion of the catalyst composition, the catalyst-deactivating composition, and the diluent, wherein the equivalent ratio of catalyst-deactivating composition to catalyst composition in the reaction product stream is from 0.10:1 to 0.70:1;

a gas/liquid phase separation system adapted to receive the reactor product stream and to form a first recycle stream and a separation system product stream; wherein the first recycle stream and the separation system product stream are essentially free of the catalyst composition; and a recycle loop adapted to recycle the first recycle stream to the oligomer synthesis reactor; wherein the first recycle stream comprises reaction medium and unreacted monomer; wherein the separator product stream comprises a majority portion of the oligomer product in the gas phase effluent; and wherein at least a portion of the separation system product stream is utilized as the oligomer product stream.

* * * * *